United States Patent
Dobbs et al.

(10) Patent No.: US 6,953,297 B2
(45) Date of Patent: Oct. 11, 2005

(54) LIQUID DISPENSER AND CLEANER

(75) Inventors: Douglas B. Dobbs, Yorba Linda, CA (US); Lluis Costa, West Covina, CA (US)

(73) Assignee: Saint-Gobain Calmar Inc., City of Industry, CA (US)

( * ) Notice: Subject to any disclaimer, the term of this patent is extended or adjusted under 35 U.S.C. 154(b) by 85 days.

(21) Appl. No.: 10/704,646

(22) Filed: Nov. 12, 2003

(65) Prior Publication Data

US 2005/0100391 A1    May 12, 2005

(51) Int. Cl.$^7$ .................. A46B 11/02; B43K 23/12; A47L 13/30; B05C 11/00
(52) U.S. Cl. .................. 401/188 R; 401/262; 401/264; 401/266
(58) Field of Search .................. 401/261–266, 401/188 R; 222/378, 379, 383.1, 385

(56) References Cited

U.S. PATENT DOCUMENTS

| | | | |
|---|---|---|---|
| 2,196,379 A * | 4/1940 | Bender ...................... 222/390 |
| 2,921,324 A | 1/1960 | Gibbons ...................... 15/134 |
| 3,032,803 A | 5/1962 | Walshauser .................. 15/578 |
| 3,256,549 A | 6/1966 | Evesque ...................... 15/552 |
| 4,757,922 A | 7/1988 | Landecker ................... 222/205 |
| 4,865,228 A | 9/1989 | Landecker ................... 222/153 |
| D358,033 S | 5/1995 | Klump ......................... D4/114 |
| 5,692,846 A | 12/1997 | Schwarzberg ............... 401/190 |
| 5,813,785 A | 9/1998 | Baudin et al. .............. 401/190 |
| 5,885,019 A | 3/1999 | Stear .......................... 401/137 |
| 6,092,952 A | 7/2000 | Eberle ........................ 401/146 |
| 6,158,674 A | 12/2000 | Humphreys ................. 239/333 |
| 6,227,740 B1 | 5/2001 | Stear et al. ................. 401/188 |
| 6,449,898 B1 * | 9/2002 | Alban ................... 47/58.1 FV |

* cited by examiner

Primary Examiner—David J. Walczak
(74) Attorney, Agent, or Firm—Dykema Gossett PLLC

(57) ABSTRACT

An applicator is adapted to be mounted on a hollow piston stem of a manually reciprocable pump dispenser for applying a cleaning liquid to a fibrous article such as fabric, rug or carpet or the like from a container of liquid to which the dispenser is mounted. The applicator has a domed outer convex rigid wall with at least one discharge port in communication with the discharge passage of the piston stem, and an outer surface of the domed wall is textured for rubbing the cleaning liquid into the fibers article during a cleaning operation. An overcap is connected to a side wall of the applicator by a hinge permitting the overcap to cover the outer surface of the domed wall when not in use. And, a container closure may be provided in telescoping relationship to the applicator which is rotatable about its central axis between lock and unlock positions.

5 Claims, 1 Drawing Sheet

LIQUID DISPENSER AND CLEANER

BACKGROUND OF THE INVENTION

This invention relates generally to an adaptor for a liquid dispenser of cleaning solution for cleaning fabric, carpet, rugs or the like, and more particularly relates to an applicator for applying the cleaning solution adapted to be coupled to a hollow piston stem of a manually actuated pump dispenser.

Known is a dispenser having an adaptor with an outer dish-shaped surface for collecting liquid products such as facial cleaners, antiseptics, polishes, etc., on depression of the plunger which is attached to a liquid pump dispenser. Typically, spot cleaning of various articles such as fabrics, carpeting, rugs or the like is carried out using a cloth or brush wetted with cleaning solution which must be manually rubbed into the article followed by blotting or wicking. In the process the liquid may spill or wet the user's hands, which are to be avoided.

There is the need for improving upon such an adaptor for use in applying a cleaning solution to a substrate such as fabric, carpet, rugs or the like which will also function to rub the cleaning solution into the article.

SUMMARY OF THE INVENTION

It is a therefore an object of the present invention to provide an adaptor/applicator for applying a cleaning liquid to fibrous articles such as fabric, carpet, rug from a container of the liquid, wherein the applicator is adapted to be coupled to the hollow stem of a piston pump of the type which is manually reciprocable, the applicator having a domed, rigid outer wall having a textured outer surface for rubbing of the applied cleaning solution to the article while pressing the domed wall against the article to be cleaned preferably spot cleaned. An overcap may be hinged to the adaptor for overlying the domed surface during periods of non-use. And, the adaptor may cooperate with a container closure in telescoping relationship for uplocking the adaptor during conditions of non-use. The adaptor is rotatable about its central axis, and is locked in an up position relative to the closure on rotation of the adaptor to a position wherein a stop thereon abuts against a shoulder on the closure to effect an up-lock of the applicator. Rotation in an opposite direction unlocks the applicator permitting its use as it is reciprocated together with the pump piston.

Other objects, advantages, and novel features of the invention will become more apparent from the following detailed description of the invention when taken in conjunction with the accompanying drawings.

DETAILED DESCRIPTION OF THE INVENTION

Figure 1:
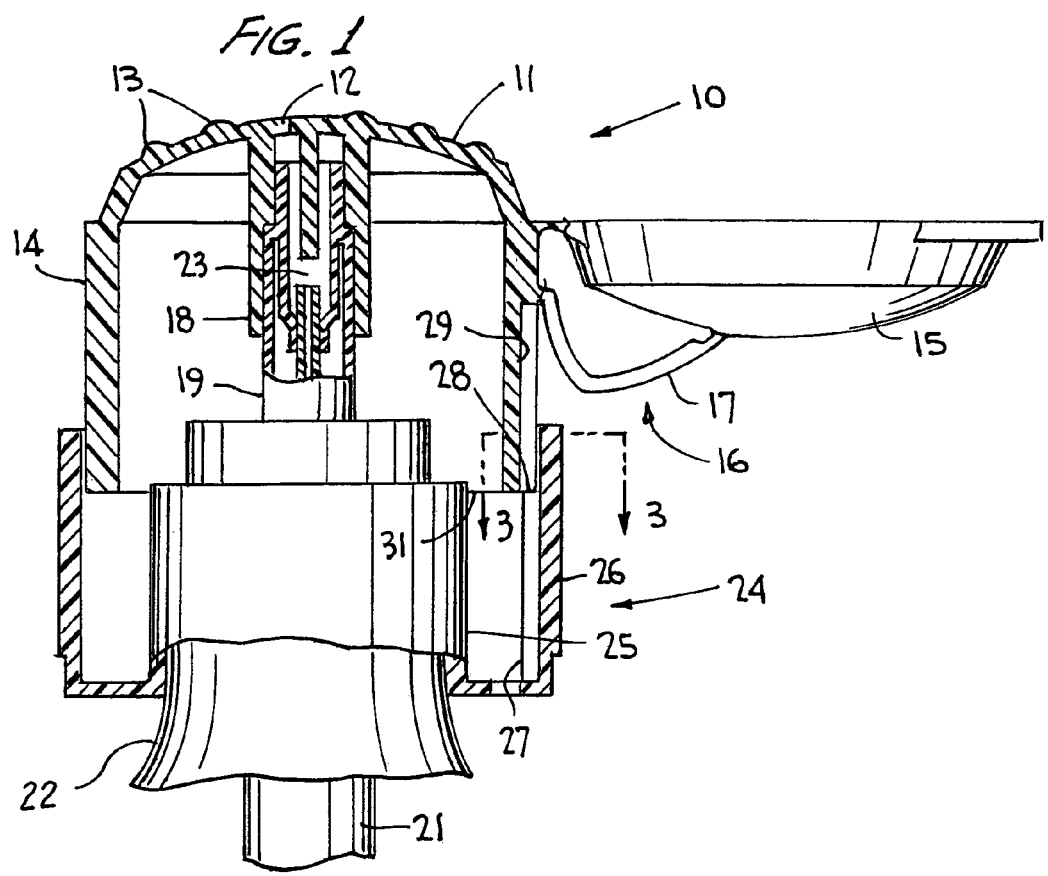
FIG. 1 is a vertical sectional view of an applicator according to the invention mounted on a partially shown manually actuated pump dispenser in side elevation.
Figure 2:
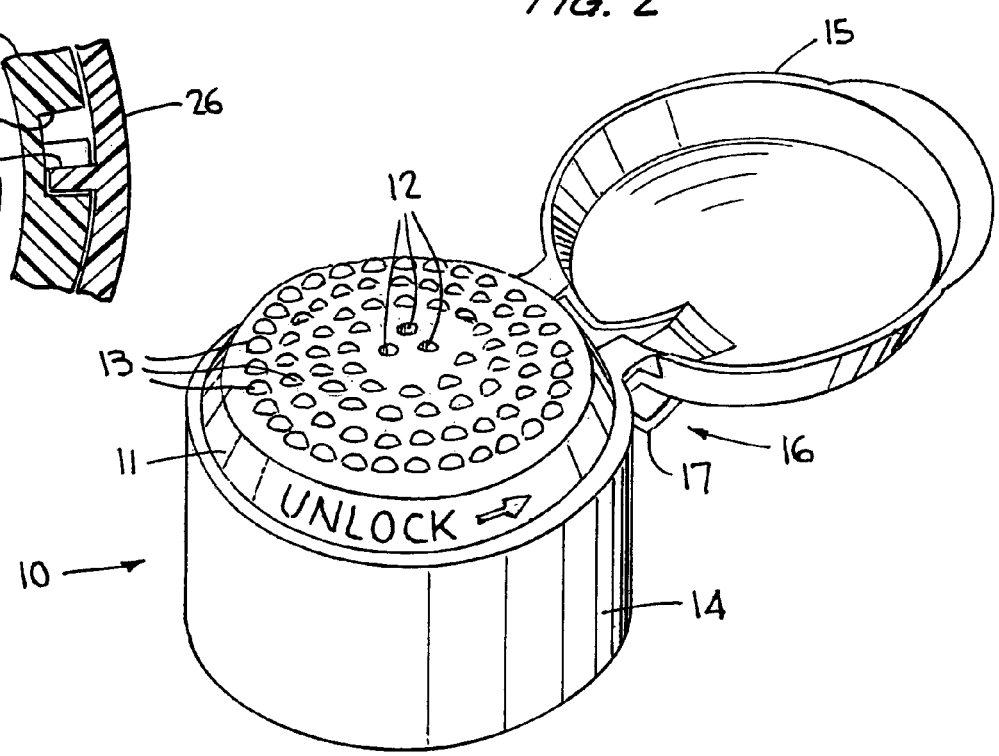
FIG. 2 is a perspective view of the applicator of FIG. 1.

Turning now to the drawings wherein like reference characters refer to like and corresponding parts throughout the several views, an applicator or an adaptor provided in carrying out the present invention and generally designated 10 in FIGS. 1 and 2 has a domed outer rigid wall 11 containing at least one discharge port 12, three of such ports being shown in FIG. 2. Certainly, fewer or more than three ports 12 may be provided without departing from the invention.

The domed outer wall has a textured outer surface shown in FIGS. 1 and 2 which may be in the form of a plurality of spaced hemispherical projections 13, although any other suitable textured (meaning roughened) outer surface of the domed outer wall can be provided in carrying out the invention. For example, a plurality of concentric circular ribs could be provided on the domed outer surface in lieu of the hemispherical projections, or a plurality of tiny or short and stubby fingers or the like could be provided in place of the hemispherical projections, or the entirety of the outer surface of the domed wall could be otherwise roughened in some known manner.

The applicator further comprises a cylindrical sidewall 14 to which the domed outer wall is integrally connected, and an overcap 15 is hingedly connected to the sidewall as at 16 for movement between the open position shown in FIGS. 1 and 2 and a closed position (not shown) which covers domed wall 11. The hinge 16 may be of the over-the-center type which, as well known in the art, operates to maintain the lid in its open position as well as in its closed and covered position. The hinge may include a strap 17 for this purpose.

The applicator likewise includes a central sleeve 18 or the like depending from outer wall 11 for mounting the applicator on hollow piston stem 19 of a hollow piston (not otherwise shown) which normally reciprocates within a pump cylinder 21 of a manually actuated pump dispenser. Any conventional pump dispenser may be provided in carrying out the invention. The pump dispenser is suitably mounted on the neck of a container 22 of liquid (which may be a cleaning solution) to be dispensed.

In operation, the user simply hinges the overcap to its open position of FIGS. 1, 2, inverts the dispenser or otherwise places the dispenser with its domed outer wall in contact with a fabric, rug or carpet or other article to be cleaned, and presses the container in a direction against the article to reciprocate the piston to thereby pressurize the cleaning the solution already in the pump chamber (not shown) so as to discharge the cleaning solution through discharge passage 23 and out through ports 12 which are in communication with the discharge passage. The discharged liquid is caused to wet the outer surface of domed outer wall 11 whereupon the operator is instructed to "beat-in" the cleaner into the fabric, rug or carpet by rubbing the applicator in a side-to-side or circular motion or the like against the article to effect cleaning of a soiled spot or area thereon. The textured or roughened outer surface of the domed wall assists in agitating the surface of the article with the cleaning solution in a simple yet highly effective manner without the need for applying the cleaning solution first to a cloth or brush as normally required for spot carpet or spot fabric cleaning. The hands of the operator thus remain out of contact with the cleaning solution and with any type of applicator cloth or brush in the process of spot cleaning. After the cleaning operation is completed, the operator simply places the erect applicator/bottle aside and recloses the overcap.

Figure 3:
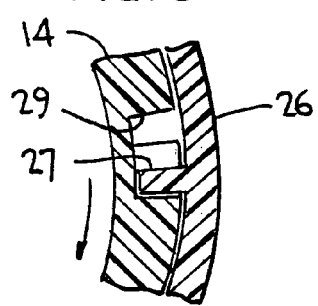
FIG. 3 is a sectional view taken substantially along the line 3-3 of FIG. 1.

In a condition of storage and shipping and other conditions of non-use, the applicator as mounted on the reciprocable piston stem should desirably be locked in place against reciprocation from its upwardly extending position of FIG. 1. For this purpose, a closure 24 is mounted on the container with which the applicator 10 cooperates. The closure includes an internally threaded cap skirt 25 threadedly secured to the neck of the container, and an upstanding circular side wall 26 spaced from the cap skirt as shown in FIG. 1 in telescoping relation to side wall 14 of the applicator. At least one axially extending lock rib 27 is provided on the inner surface of wall 26 presenting a stop shoulder 28 at its upper end. A corresponding axially extending groove 29 is formed in the outer surface of side wall 14 of the applicator such that in an unlocked position groove 29 is placed into alignment with lock rib 27. Applicator 10 is, together with piston stem 19 to which it is mounted, capable of rotating about its central axis such that when rotated in the direction of the arrows of FIGS. 2 and 3, groove 29 will be shifted into alignment with rib 27 to thereby facilitate reciprocation of the applicator relative to the closure. Upon shifting the applicator into the lock position of FIG. 3, rib 27 lies in the path of the lower edge 31 of wall 14. Edge 31 will simply abut against stop 28 in this locked position preventing applicator and piston reciprocation.

It can be seen that a simple and efficient yet highly effective applicator of liquid such as a cleaning solution for the spot or area cleaning of an article such as fabric, carpet or rug or the like has been devised which eliminates the need for handling the cleaning solution as before as with a brush or cloth to effect spot or area cleaning. The operator's hands never contact the cleaning solution thereby avoiding the need for wearing cleaning gloves or the like. Besides, only a metered amount of cleaning solution is dispensed onto the outer surface of the domed wall 11 when the applicator is depressed relative to the container, and the roughened outer surface of the domed wall functions to abrade or agitate the fibers of the article to be cleaned with the cleaning solution while the applicator head is rubbed against the article in a most efficient and effective manner. The applicator with its domed head is of a rigid material to avoid collapse of the domed head during use and can therefore be of a polypropylene material or the like. The outer surface of the domed head is roughened or textured by the provision of a plurality of hemispherical projections given as an example, although roughened surfaces of other types may be provided as the full equivalent to the hemispherical projections, without departing from the invention.

Obviously, many other modifications and variations of the present invention are made possible in the light of the above teachings. It is therefore to be understood that within the scope of the appended claims, the invention may be practiced otherwise than as specifically described.

What is claimed is:

1. A dispenser for applying a cleaning liquid to a fibrous article such as fabric, carpet, or rug, from a container of the liquid, comprising a manually actuated pump having a hollow piston stem defining a discharge passage, an applicator mounted on said piston stem for reciprocation together therewith, said applicator comprising a domed outer rigid wall having at least one discharge port in communication with said discharge passage to permit the liquid to flow on to an outer surface of said wall upon reciprocation of said applicator, and said domed outer wall having a textured outer surface for rubbing the liquid into the fibers of the article during a cleaning operation, wherein said applicator has a cylindrical sidewall connected to said domed wall, and an overcap hinged to said sidewall and pivotable in a first direction for covering said domed wall in a condition of non-use of the dispenser, said overcap being pivotable in a second opposite direction for substantially exposing said applicator to enable said applicator to contact the fibrous article without intereference from said overcap, and wherein lock means is provided for locking the actuator in a condition of non-use of the dispenser, the applicator having a depending cylindrical sidewall in telescoping relation to an upstanding cylindrical skirt of the lock means, axially extending rib and groove means acting between the sidewall and the skirt for locking and unlocking the applicator relative to the skirt upon applicator rotation about a central axis thereof.

2. The dispenser according to claim 1, wherein the overcap is connected to the sidewall by an over-the-center hinge for maintaining the overcap in an uncovered position during use of the dispenser, and for maintaining the overcap covered over the domed wall during non-use.

3. The dispenser according to claim 1, wherein said domed outer wall is provided with a plurality of spaced hemispherical projections comprising said textured surface.

4. An adaptor for applying a cleaning liquid to a fibrous article such as fabric, rug or carpet from a container of the liquid, comprising an applicator adapted to be mounted on a hollow piston stem of a manually reciprocable pump dispenser, the applicator having a domed outer convex rigid wall having at least one open discharge port for directing liquid to an outer surface of said domed wall, said outer surface being textured for rubbing liquid into the fibers of the article during use, the applicator having a cylindrical side wall to which the domed wall is connected, and an overcap connected to the sidewall by a hinge permitting the overcap to be pivoted in a first direction to cover the outer surface of the domed wall during non-use, said overcap being pivotable in a second opposite direction for substantially exposing said applicator to enable said applicator to contact the fibrous article without intereference from said overcap, wherein the hinge comprises an over-the-center hinge capable of maintaining the overcap in open and closed positions relative to the domed outer surface, said adaptor further comprising a container closure in telescoping relationship to the applicator for relative reciprocating movement, the applicator being rotatable about a central axis thereof, lock means acting between the applicator and the closure preventing movement of the applicator toward the closure in at least one selected rotary position of the applicator, wherein the lock means comprises an axial rib on one of the applicator and the closure and an axial groove on the other of the applicator and the closure, the rib providing a stop preventing the movement in the one rotary position.

5. The adaptor according to claim 4, wherein the textured outer surface comprises a plurality of spaced hemispherical projections.

* * * * *